US012796919B2

(12) United States Patent
Tal et al.

(10) Patent No.: US 12,796,919 B2
(45) Date of Patent: Nov. 17, 2026

(54) RETINAL IMAGING-BASED EYE ACCOMMODATION DETECTION

(71) Applicant: Apple Inc., Cupertino, CA (US)

(72) Inventors: Eran Tal, Petach Tivka (IL); Ariel Lipson, Tel Aviv (IL)

(73) Assignee: Apple Inc., Cupertino, CA (US)

( * ) Notice: Subject to any disclaimer, the term of this patent is extended or adjusted under 35 U.S.C. 154(b) by 515 days.

(21) Appl. No.: 18/027,400

(22) PCT Filed: Sep. 10, 2021

(86) PCT No.: PCT/US2021/049778
§ 371 (c)(1),
(2) Date: Mar. 21, 2023

(87) PCT Pub. No.: WO2022/066429
PCT Pub. Date: Mar. 31, 2022

(65) Prior Publication Data

US 2023/0329549 A1 Oct. 19, 2023

Related U.S. Application Data

(60) Provisional application No. 63/081,498, filed on Sep. 22, 2020.

(51) Int. Cl.
*A61B 3/12* (2006.01)
*A61B 3/00* (2006.01)
*A61B 3/113* (2006.01)

(52) U.S. Cl.
CPC ................ *A61B 3/12* (2013.01); *A61B 3/005* (2013.01); *A61B 3/113* (2013.01)

(58) Field of Classification Search
CPC .......... G02B 27/017; G02B 2027/0127; G02B 2027/0138; G02B 2027/0187;
(Continued)

(56) References Cited

U.S. PATENT DOCUMENTS 4,778,268 A 10/1988 Randle
10,248,194 B2 4/2019 Swedish et al.
(Continued)

FOREIGN PATENT DOCUMENTS

CH 697949 B1 3/2009
DE 19950791 A1 5/2001
JP 2006-42952 A 2/2006

OTHER PUBLICATIONS

PCT) European Patent Office, International Search Report and Written Opinion, International Application No. PCT/US2021/049778, 15 pages, Dec. 20, 2021.
(Continued)

*Primary Examiner* — Nelson M Rosario
(74) *Attorney, Agent, or Firm* — Thompson Hine LLP

(57) ABSTRACT

Some implementations disclosed herein provide systems, methods (200), and devices (10) that use a retinal imaging technique to assess a user's eye (45) accommodation (i.e., focus) during use of an electronic device (10), e.g., in real time. One or more light sources (322*a-d,* 1022*a-d*) produce one or more illuminated spots (320, 420, 520, 620) on the retina that are detectable via a sensor (324, 1024). The size and shape of the spot(s) (320, 420, 520, 620) depend upon the eye accommodation/focus and thus are used to identify an accommodation/focus change or measure the eye's accommodation/focus. Eye accommodation may be determined in real time while a user is viewing, interacting with, or otherwise experiencing electronic content via the electronic device.

26 Claims, 4 Drawing Sheets

(58) Field of Classification Search
CPC .......... G06F 3/012; G06F 3/013; G06F 3/147; G09G 3/001; G09G 3/32; G09G 3/36; G09G 5/391; G09G 2320/0261; G09G 2354/00; A61B 3/10
See application file for complete search history.

(56) References Cited

U.S. PATENT DOCUMENTS

| | | | |
|---|---|---|---|
| 2007/0159600 | A1 | 7/2007 | Gil |
| 2008/0304012 | A1 | 12/2008 | Kwon et al. |
| 2012/0307208 | A1 | 12/2012 | Trousdale |
| 2015/0271478 | A1 | 9/2015 | Zhou |
| 2016/0012291 | A1 | 1/2016 | Cleland et al. |
| 2016/0026253 | A1 * | 1/2016 | Bradski ................ H04N 13/128 345/8 |
| 2016/0212401 | A9 * | 7/2016 | Zhou ....................... G06F 3/017 |
| 2017/0160518 | A1 | 6/2017 | Lanman et al. |
| 2017/0160798 | A1 | 6/2017 | Lanman et al. |
| 2017/0277257 | A1 | 9/2017 | Ota et al. |
| 2018/0164535 | A1 | 6/2018 | Brown |
| 2018/0292896 | A1 | 10/2018 | Hicks et al. |
| 2020/0004327 | A1 | 1/2020 | Wang et al. |
| 2020/0057495 | A1 * | 2/2020 | Chae .................. G06F 3/04842 |
| 2020/0241308 | A1 | 7/2020 | Danziger et al. |

OTHER PUBLICATIONS

European Patent Office, Communication Pursuant to Article 94(3) EPC, European Patent Application No. 21787155.7, 8 pages, Nov. 19, 2025.
China National Intellectual Property Administration, Second Office Action issued in Chinese Patent Application No. 202180078144.7 dated Mar. 27, 2026 with English translation (20 pages).
China National Intellectual Property Administration, Notification to Grant Patent Right for Invention issued in Chinese Patent Application No. 202180078144.7 dated Jun. 10, 2026 with English translation (Five (5) pages).
Guojian, Laser Speckles and Human Ocular Ametropia, Journal of Hefei University of Technology, Issue 3, 1983 with machine English translation (20 pages).

* cited by examiner

RETINAL IMAGING-BASED EYE ACCOMMODATION DETECTION

CROSS-REFERENCE TO RELATED APPLICATIONS

This patent application is the national stage of International Application No. PCT/US2021/049778 filed on Sep. 10, 2021, which claims the benefit of U.S. Provisional Patent Application No. 63/081,498 filed on Sep. 22, 2020, entitled “RETINAL IMAGING-BASED EYE ACCOMMODATION DETECTION,” each of which is incorporated herein by this reference in its entirety.

TECHNICAL FIELD

The present disclosure generally relates to providing improved user experiences on electronic devices, and in particular, to systems, methods, and devices that detect eye accommodation (i.e., focus) during use of electronic devices.

BACKGROUND

Various eye tracking techniques exist. For example, some gaze tracking techniques are based on detecting reflections on outer portions of the eye. Light is directed toward an eye to cause detectable reflections on the pupil and cornea and these reflections are tracked by a camera to determine gaze direction, for example, by determining a vector between the cornea and pupil that corresponds to gaze direction. Existing eye tracking techniques may not provide adequate tracking of eye accommodation (i.e., focus).

SUMMARY

Some implementations disclosed herein provide systems, methods, and devices that use a retinal imaging technique to assess a user’s eye accommodation (i.e., focus) during use of an electronic device, e.g., in real time. One or more light sources direct lights toward one or more spots on the retina that are detectable via a sensor. The size and shape of the spot(s) depend upon the eye accommodation/focus and thus are used to identify an accommodation/focus change or measure the eye’s accommodation/focus. Eye accommodation may be determined in real time while a user is viewing, interacting with, or otherwise experiencing electronic content via the electronic device.

Some implementations involve a method that is performed via a processer executing instructions stored in a non-transitory memory of an electronic device. Such a method may involve, at an electronic device having a processor and a light source, producing light (e.g., infrared or visible light) using the light source to direct light toward a spot on a retina of an eye. For example, one or more collimated illuminators may be used to direct light toward one or more spots on the retina. The light sources may be oriented in an off-axis manner relative to an axis of the eye. The method receives sensor data (e.g., an image) at a sensor (e.g., a camera). The sensor data corresponds to the illuminated spot on the retina. For example, the sensor data may include one or more camera images having image portions, e.g., pixels that correspond to a retinal appearance including light reflected at an illuminated spot.

The method determines an eye accommodation characteristic based on the sensor data. In some implementations, the eye accommodation characteristic is determined based on a size or a position of the illuminated spot on the retina. Determining the eye accommodation characteristic may involve detecting a change in accommodation or finding an estimate (e.g., a numerical value representing) the accommodation of the eye. In some implementations, determining the eye accommodation characteristic involves comparing an image of the retina to a previous image of the retina to identify a change in size and/or position of an illuminated spot. In some implementations, a spot is identified (e.g., its size, shaped, and/or position) and/or distinguished from other less-illuminated portions of the retina. A spot may be identified via an algorithm (e.g. based on a threshold) and/or using a machine learning (ML) model. A ML model may be used to assess/compare the size and/or position of the spot and/or a relationship between multiple spots.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1:
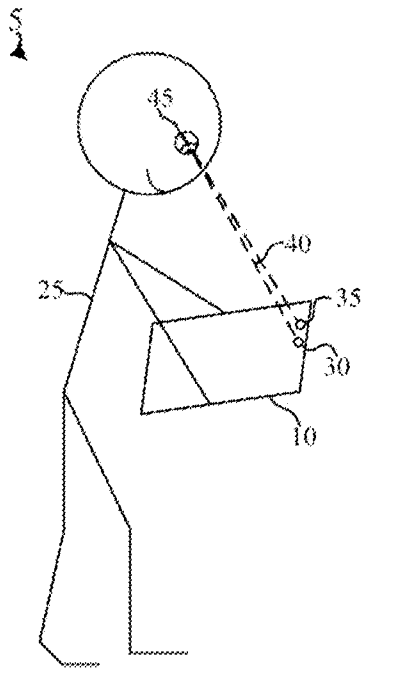
FIG. 1 illustrates a device providing a user interface and obtaining data corresponding to a user while the user is using an electronic device.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

FIG. 1 illustrates an example in which electronic device 10 is used in physical environment 5. A physical environment refers to a physical world that people can interact with and/or sense without the aid of electronic systems. Physical environments, such as a physical park, include physical articles, such as physical trees, physical buildings, and physical people. People can directly sense and/or interact with the physical environment, such as through sight, touch, hearing, taste, and smell.

In the example of FIG. 1, the device 10 is illustrated as a single device. Some implementations of the device 10 are hand-held. For example, the device 10 may be a mobile phone, a tablet, a laptop, and so forth. In some implementations, the device 10 is worn by a user. For example, the device 10 may be a watch, a head-mounted device (HMD), and so forth. In some implementations, functions of the device 10 are accomplished via two or more devices, for example additionally including an optional base station. Other examples include a laptop, desktop, server, or other such device that includes additional capabilities in terms of power, CPU capabilities, GPU capabilities, storage capabilities, memory capabilities, and the like. The multiple devices that may be used to accomplish the functions of the device 10 may communicate with one another via wired or wireless communications.

In some implementations, the device 10 includes an eye tracking system for detecting eye position and eye movements. The eye tracking system may include one or more illuminators 30 (e.g., one or more infrared (IR) light-emitting diodes (LEDs)) that emit light 40 that is reflected off of eye 45 and captured via sensor 35 (e.g., a near-IR (NIR) camera). In one example, the one or more illuminators 30 of the device 10 may emit NIR light directed toward one or more spots on the retina of the eye 45 of the user 25 and the sensor 35 capture images of the eye 45 of the user 25 including the illuminated spot. In some implementations, images captured by the eye tracking system may be analyzed to detect position and movements of the eyes of the user 25, to detect other information about the eyes such as gaze direction, and/or to detect accommodation/focus of the eye. Moreover, the point of gaze estimated from the eye tracking images may enable gaze-based interaction with content.

In some implementations, the device 10 has a user interface (e.g., a graphical user interface GUI), one or more processors, memory and one or more modules, programs or sets of instructions stored in the memory for performing multiple functions. In some implementations, the user 25 interacts with the user interface through finger contacts and gestures on the touch-sensitive surface. In some implementations, the functions include image editing, drawing, presenting, word processing, website creating, disk authoring, spreadsheet making, game playing, telephoning, video conferencing, e-mailing, instant messaging, workout support, digital photographing, digital videoing, web browsing, digital music playing, and/or digital video playing. Executable instructions for performing these functions may be included in a computer readable storage medium or other computer program product configured for execution by one or more processors.

Figure 2:
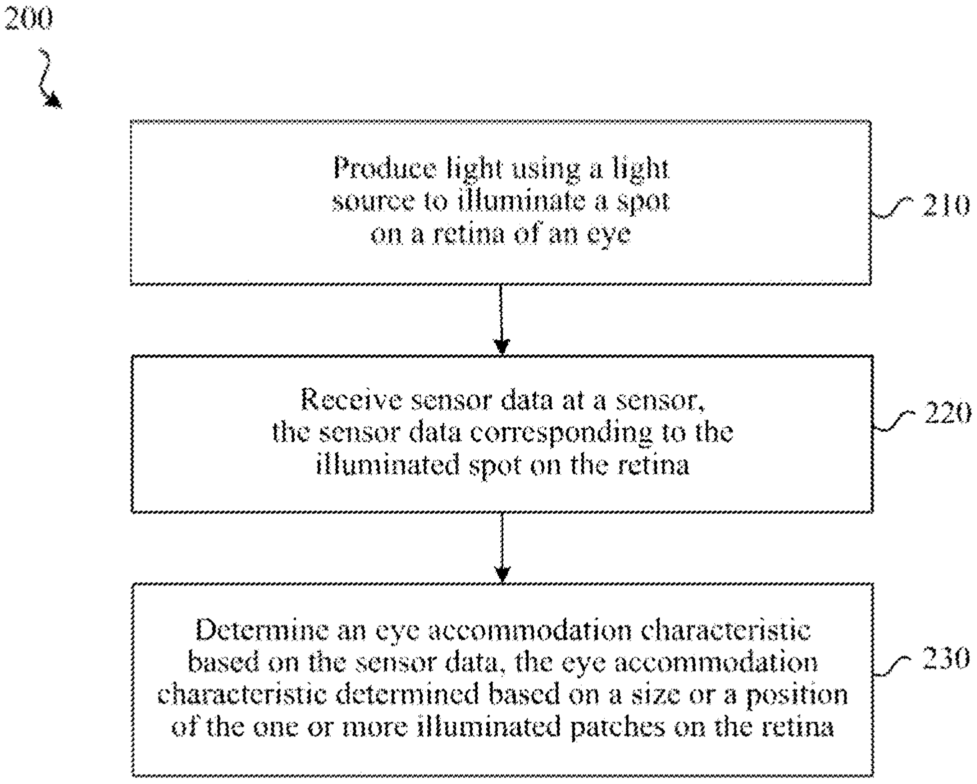
FIG. 2 is a flow chart illustrating an exemplary method of assessing a user’s eye accommodation (i.e., focus) using a retinal imaging technique according to some implementations.

FIG. 2, in accordance with some implementations, is a flowchart representation of a method 200 of using a retinal imaging technique to assess a user's eye accommodation (i.e., focus) during use of an electronic device. In some implementations, the method 200 is performed by one or more devices (e.g., device 10). The method 200 can be performed at a mobile device, HMD, desktop, laptop, or server device. In some implementations, the method 200 is performed by processing logic, including hardware, firmware, software, or a combination thereof. In some implementations, the method 200 is performed by a processor executing code stored in a non-transitory computer-readable medium (e.g., a memory).

At block 210, the method 200 produces light (e.g., infrared or visible light) using a light source toward a spot on a retina of an eye. For example, one or more collimated illuminators may be used to direct light toward one or more spots on the retina. In some implementations, multiple light sources may simultaneously direct light toward multiple, separate spots on the retina. In some implementations, the light source has collimated illuminators that simultaneously direct light toward multiple spots on the retina. In some implementations, the light source provides light in a variety of different wavelengths and/or polarization states.

The light source(s) may be oriented in an off-axis manner relative to an axis of the eye. Using an off-axis light source may increase the impact of differences in accommodation upon one or more spots illuminated on a retina, i.e., the more off axis the greater the change in size and/or location of a spot as eye accommodation changes. In some implementations, off-axis illumination may facilitate use of a dedicated camera for accommodation detection without interfering with the retina eye tracking.

At block 220, the method 200 receives sensor data (e.g., an image) at a sensor (e.g., a camera). The sensor data corresponds to the illuminated spot on the retina. For example, the sensor data may include one or more camera images having image portions, e.g., pixels that correspond to a retinal appearance including light reflected at an illuminated spot. In some implementations, the sensor data corresponds to multiple spots.

At block 230, the method 200 determines an eye accommodation characteristic based on the sensor data. In some implementations, the eye accommodation characteristic is determined based on a size or a position of the illuminated spot on the retina. Eye accommodation may be determined in real time during presentation of content via the electronic device, e.g., while a user is viewing, interacting with, or otherwise experiencing electronic content via the electronic device. In an implementation in which multiple spots are illuminated, one or more of those spots may be used to determine the eye accommodation characteristic. In one example, one of multiple spots is selected for use in determining the eye accommodation characteristic based on an attribute (e.g., size, shape, position, etc.) of the spot relative to attributes of other spots.

Determining the eye accommodation characteristic may involve detecting a change in accommodation or finding an estimate (e.g., a numerical value representing) the accommodation of the eye. In some implementations, determining the eye accommodation characteristic involves comparing an image of the retina to a previous image of the retina to identify a change in size and/or position of an illuminated spot or multiple illuminated spots. In some implementations, an eye accommodation characteristic is determined based on a distance between two or more simultaneously illuminated spots on a retina or a size of an illuminated spot's pattern on a retina.

In some implementations, a spot is identified (e.g., its size, shaped, and/or position) and/or distinguished from other less-illuminated portions of the retina. A spot may be identified via an algorithm (e.g. based on a threshold) and/or using a machine learning (ML) model. A ML model may be used to assess/compare the size and/or position of the spot and/or a relationship between multiple spots. In one example, thresholds (e.g., thresholds of pixel brightness of pixels, relationship to nearby pixels, etc.) are used to identify a spot and/or its size, position, and/or other detectable attributes. One example of this is to vary the divergence of a point illumination source or sources until the smallest possible spot appears in the imaging camera. When that occurs and/or is detected, the eye accommodation exactly cancels a calibrated divergence of the source. Examples of machine learning models include but are not limited to neural networks (e.g., an artificial neural networks), decision trees, support vector machines, or Bayesian networks.

In some implementations, the light source provides light in a variety of different wavelengths and/or polarization states and these differences are used to aid interpretation of an image obtained via a sensor, e.g., by facilitating identification of a spot (e.g., its size, shaped, and/or position) and/or distinguished a spot from other portions of the retina.

Eye accommodation determinations may be used for a variety for a variety of purposes. In some implementations, for example, method 200 further involves determining an object upon which the eye is focused based on the eye accommodation characteristic. In some implementations, method 200 further involves improving user comfort during a user experience, for example, by positioning a virtual object in a graphical environment at a depth determined based on the eye accommodation characteristic. For example, a virtual object may be placed at approximately the depth/distance from the user that the user is focused upon.

Eye accommodation may be used to provide information, messages, feedback, or to otherwise enhance content provided to a user. For example, content may be highlighted or distinguished based on detecting what a user is focused upon. In some implementations, method 300 further involves tracking a gaze direction of the eye based on the eye accommodation characteristic. Gaze direction may be used to identify real or virtual object upon which a user is focusing.

In some implementations, the method 300 further involves changing an optical focus of an outward facing camera based on a determined eye accommodation characteristic. Information obtained from such a camera include image data that can be presented to the user, modified and presented by the user, or otherwise used by the method 300 to provide content to the user.

In some implementations, eye accommodation is used to enhance foveated rendering provided on a display. For example, eye accommodation may be used to determine what the user is focused upon or where, relative to a display, a user is focusing. Such information may be used to configure the display for optimal or efficient display, for example, by adjusting display settings for different portions of the display accordingly.

In some implementations, eye accommodation and/or an identification of what a user is focused upon is used to improve communication, efficiency, or other aspects of the system that provides the method 300. For example, content associated with an object (e.g., augmentations, supplemental information, related objects, etc.) may be fetched or processed based on determining that the user is focused upon the object.

Figure 3:
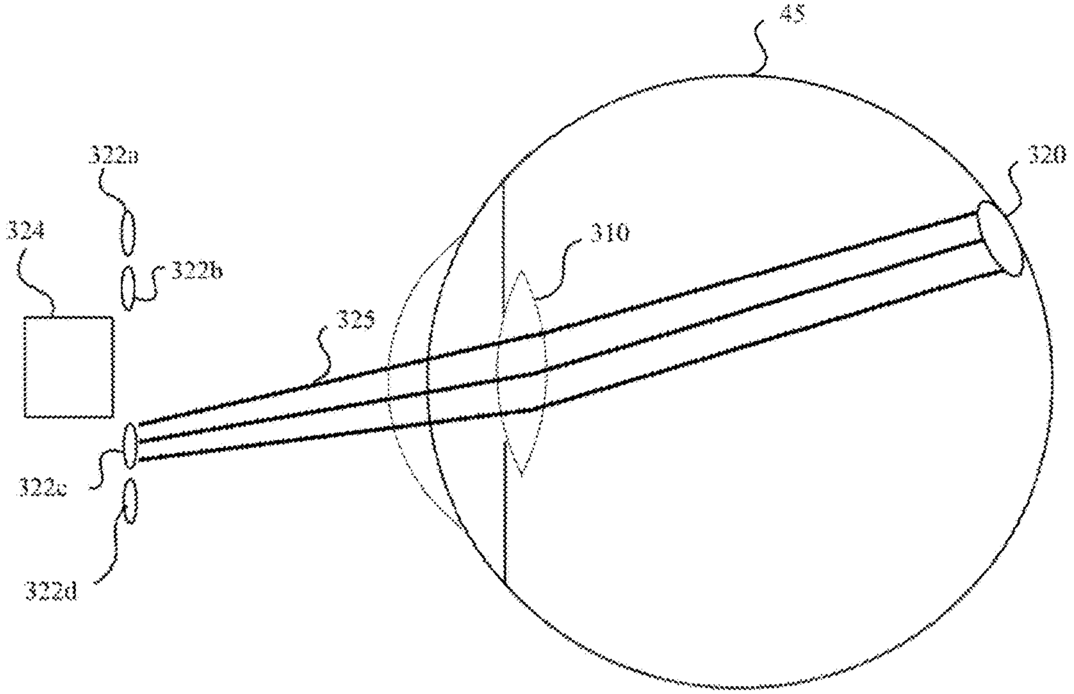
FIG. 3 illustrates one or more illuminators directing light toward a spot on a retina of an eye in a first accommodation/focus state according to some implementations.

FIG. 3 illustrates a one or more illuminators 322*a-d* directing light toward a spot 320 on a retina of eye 45 in a first accommodation/focus state. In this example, the one or more illuminators 322*a-d* direct light 325 toward a retina portion of eye 45. The light 325 travels through the lens 310 to produce a spot 320 on the retina of the eye 45. Sensor 324 captures an image of the retina of the eye 45 including an image of the spot 320.

Figure 4:
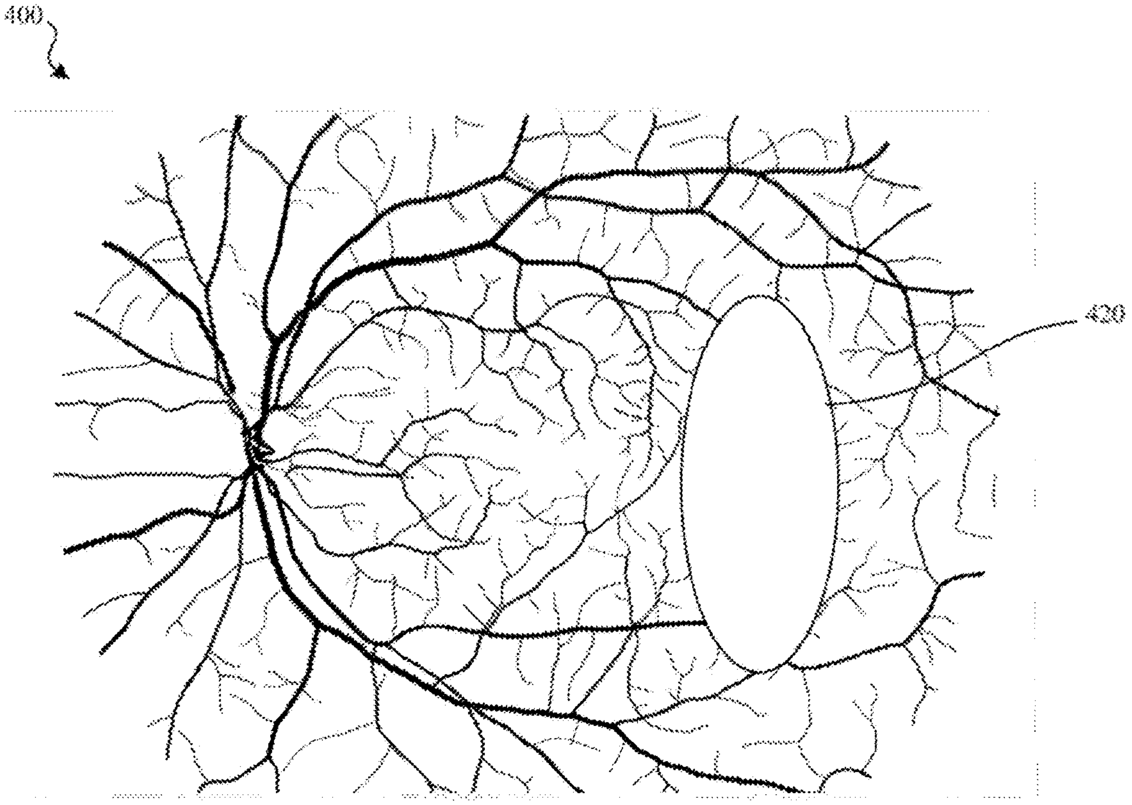
FIG. 4 illustrates an image of the retina including the spot illuminated in FIG. 3.

FIG. 4 illustrates an image 400 of the retina including a depiction 420 of the spot 320 illuminated in FIG. 3. An eye accommodation characteristic is determined based on a size or a position of the depiction 420 of the spot 320, e.g., relative to blood vessels and other aspects of the retina depicted in the image 400. Determining the eye accommodation characteristic may involve determining an estimate (e.g., a numerical value such as 50 diopters) the accommodation of the eye 45, for example, based on the relative size and/or position of the depiction 420 of the spot 320 relative to blood vessels and other aspects of the retina depicted in the image 400.

Figure 5:
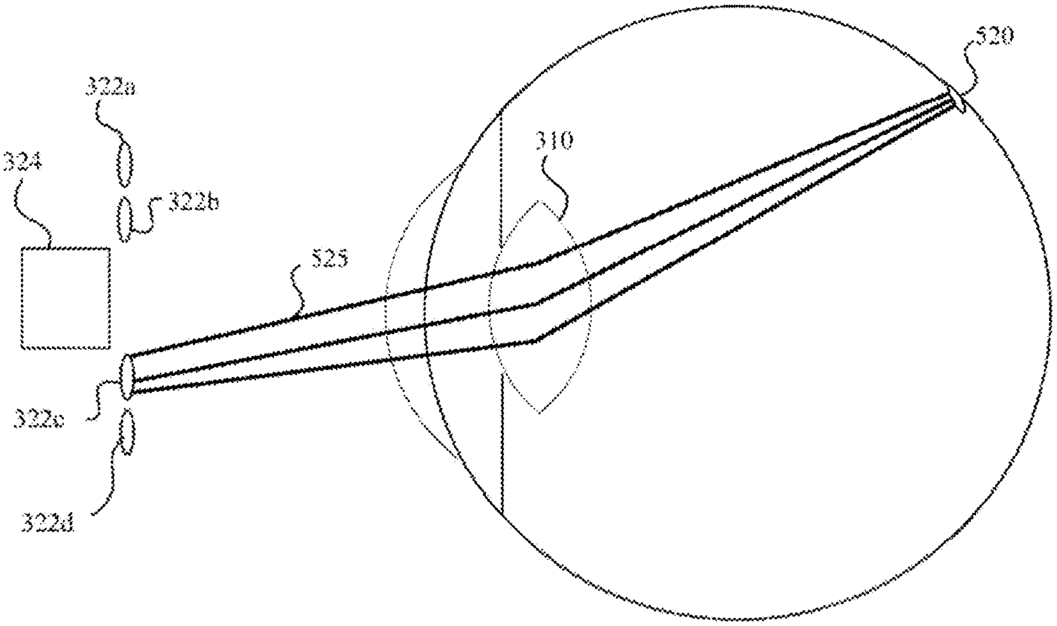
FIG. 5 illustrates the one or more illuminators of FIG. 3 directing light toward a spot on the retina of the eye in a second accommodation/focus state according to some implementations.

FIG. 5 illustrates the one or more illuminators 322*a-d* of FIG. 3 directing light toward a different spot 520 on the retina of the eye 45 in a second accommodation/focus state. In this example, the one or more illuminators 322*a-d* direct light 525 toward a retina portion of eye 45. The light 525 travels through the lens 310 to produce a spot 520 on the retina of the eye 45. Since the lens 310 has a different shape than in FIG. 3, the spot 520 differs in size and location relative to the spot in FIG. 3. Sensor 324 captures an image of the retina of the eye 45 including an image of the spot 520.

Figure 6:
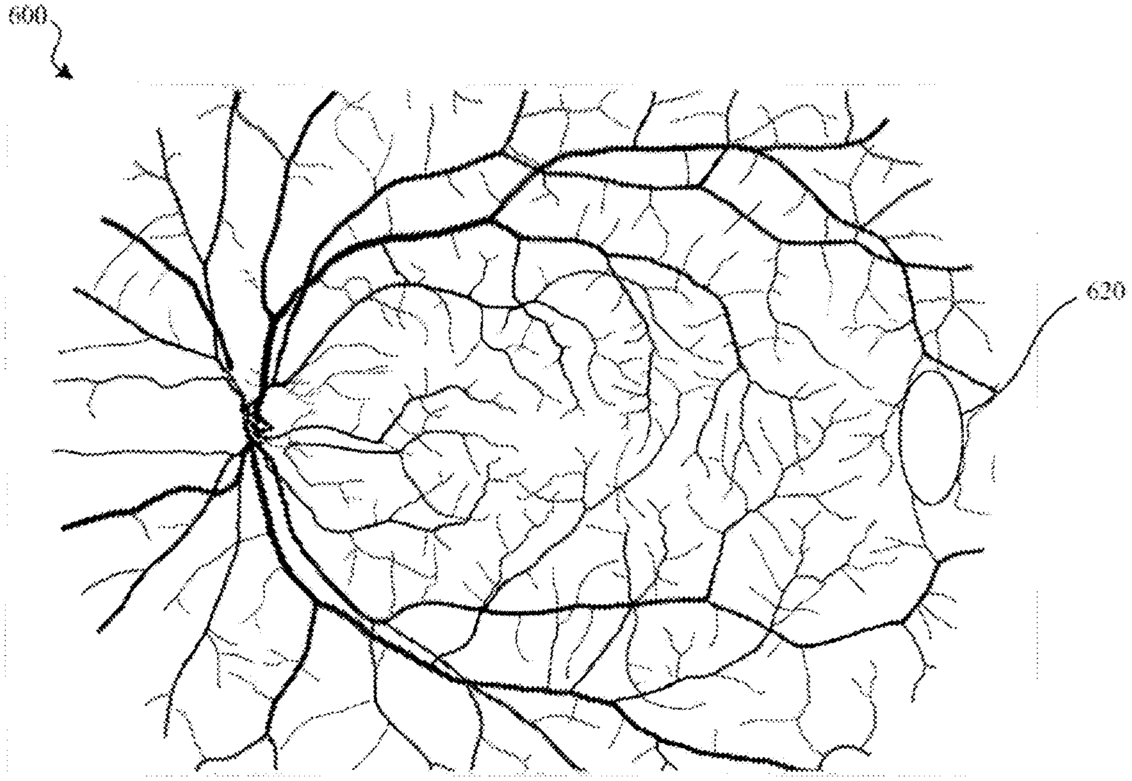
FIG. 6 illustrates an image of the retina including the spot illuminated in FIG. 5.

FIG. 6 illustrates an image 600 of the retina including a depiction 620 of the spot 520 illuminated in FIG. 5. In some implementations, an eye accommodation characteristic is determined based on a size or a position of the depiction 620 of the spot 320, e.g., relative to blood vessels and other aspects of the retina depicted in the image 600. Determining the eye accommodation characteristic may involve determining an estimate (e.g., a numerical value representing) the accommodation of the eye 45, for example, based on the relative size and/or position of the depiction 620 of the spot 520 relative to blood vessels and other aspects of the retina depicted in the image 400. In some implementations, an eye accommodation characteristic is determined based on a relative size or a relative position of the depiction 620 of the spot 520 compared to that of the depiction 420 of the spot 320, e.g., comparing data from two different points in time and accommodative states by comparing aspects of image 400 and image 600.

Figure 7:
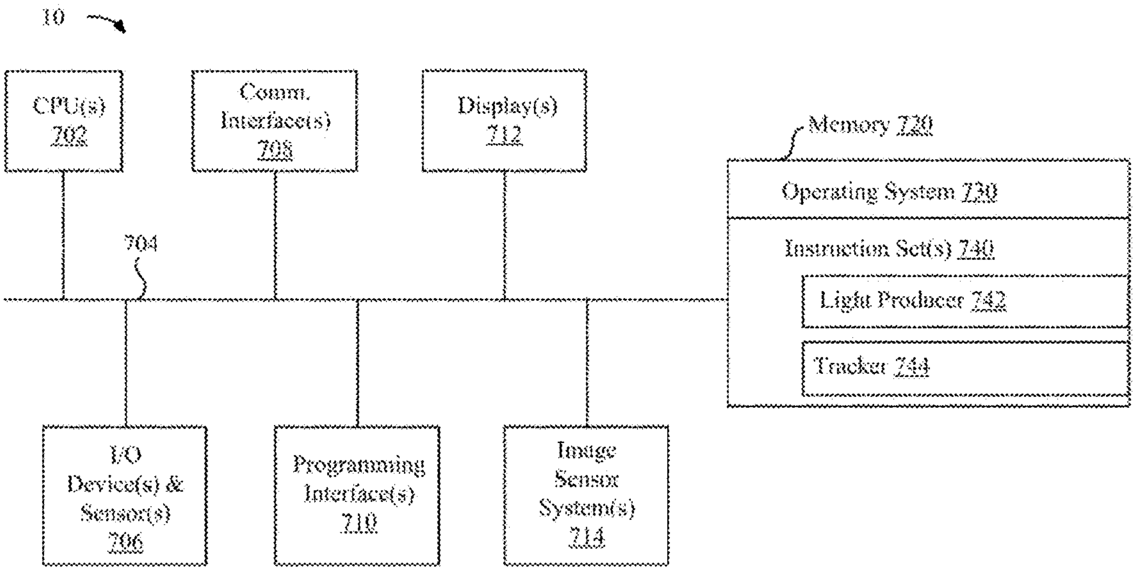
FIG. 7 is a block diagram illustrating device components of an exemplary device according to some implementations.

FIG. 7 is a block diagram of an example of a device 10 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 10 includes one or more processing units 702 (e.g., microprocessors, ASICs, FPGAs, GPUs, CPUs, processing cores, and/or the like), one or more input/output (I/O) devices and sensors 706, one or more communication interfaces 708 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, and/or the like type interface), one or more programming (e.g., I/O) interfaces 710, one or more displays 712, one or more interior and/or exterior facing image sensor systems 714, a memory 720, and one or more communication buses 704 for interconnecting these and various other components.

In some implementations, the one or more communication buses 704 include circuitry that interconnects and controls communications between system components. In some implementations, the one or more I/O devices and sensors 706 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, electroencephalography (EEG) sensor, electrocardiography (ECG) sensor, electromyography (EMG) sensor, functional near infrared spectroscopy signal (fNIRS) sensor, skin conductance sensor, or image sensor, e.g., for pupillary response, etc.), one or more microphones, one or more speakers, a haptics engine, one or more depth sensors (e.g., a structured light, a time-of-flight, or the like), and/or the like.

In some implementations, the one or more displays 712 are configured to present a user experience to the user 25. In some implementations, the one or more displays 712 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), microelectromechanical system (MEMS), a retinal projection system, and/or the like display types. In some implementations, the one or more displays 712 correspond to diffractive, reflective, polarized, holographic, etc. waveguide displays. In one example, the device 10 includes a single display. In another example, the device 10 includes a display for each eye of the user 25, e.g., an HMD. In some implementations, the one or more displays 712 are capable of presenting extended reality (XR) content, e.g., augmented reality content, virtual reality content, etc.

In some implementations, the one or more image sensor systems 714 are configured to obtain image data that corresponds to at least a portion of the face of the user 25 that includes the eyes of the user 25. For example, the one or more image sensor systems 714 include one or more RGB camera (e.g., with a complimentary metal-oxide-semiconductor (CMOS) image sensor or a charge-coupled device (CCD) image sensor), monochrome camera, IR camera, event-based camera, and/or the like. In various implementations, the one or more image sensor systems 714 further include illumination sources that emit light upon the portion of the face of the user 25, such as a flash or a glint source.

The memory 720 includes high-speed random-access memory, such as DRAM, SRAM, DDR RAM, or other random-access solid-state memory devices. In some implementations, the memory 720 includes non-volatile memory, such as one or more magnetic disk storage devices, optical disk storage devices, flash memory devices, or other non-volatile solid-state storage devices. The memory 720 optionally includes one or more storage devices remotely located from the one or more processing units 702. The memory 720 comprises a non-transitory computer readable storage medium. In some implementations, the memory 720 or the non-transitory computer readable storage medium of the memory 720 stores the following programs, modules and data structures, or a subset thereof including an optional operating system 720 and instruction set(s) 740.

The operating system 730 includes procedures for handling various basic system services and for performing hardware dependent tasks. In some implementations, the instruction set(s) 740 is/are configured to implement gaze tracking and/or related features. To that end, in various implementations, the instruction set(s) 740 includes a light producer 742 and a tracker 744.

In some implementations, the light producer 742 is configured to control the production of illuminated spots on the retina of a user, for example, by determining when and/or how an illumination source will be operated to produce such spots. To these ends, in various implementations, the light producer 742 includes instructions and/or logic therefor, and heuristics and metadata therefor.

In some implementations, the tracker 744 is configured to determine accommodation/focus of an eye based on sensor data. This may involve detecting one or more illuminated spots on the retina via a sensor and using the size and/or shape of the spot(s) to determine an eye accommodation/focus characteristic, e.g., state, changes, etc. To these ends, in various implementations, the tracker 744 includes instructions and/or logic therefor, and heuristics and metadata therefor.

Although the units and modules of FIG. 7 are shown as residing on a single device (e.g., the device 10), it should be understood that in other implementations, any combination of these units may be located in separate computing devices.

Moreover, FIG. 7 is intended more as functional description of the various features which are present in a particular implementation as opposed to a structural schematic of the implementations described herein. As recognized by those of ordinary skill in the art, items shown separately could be combined and some items could be separated. For example, some functional modules shown separately in FIG. 8 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 8:
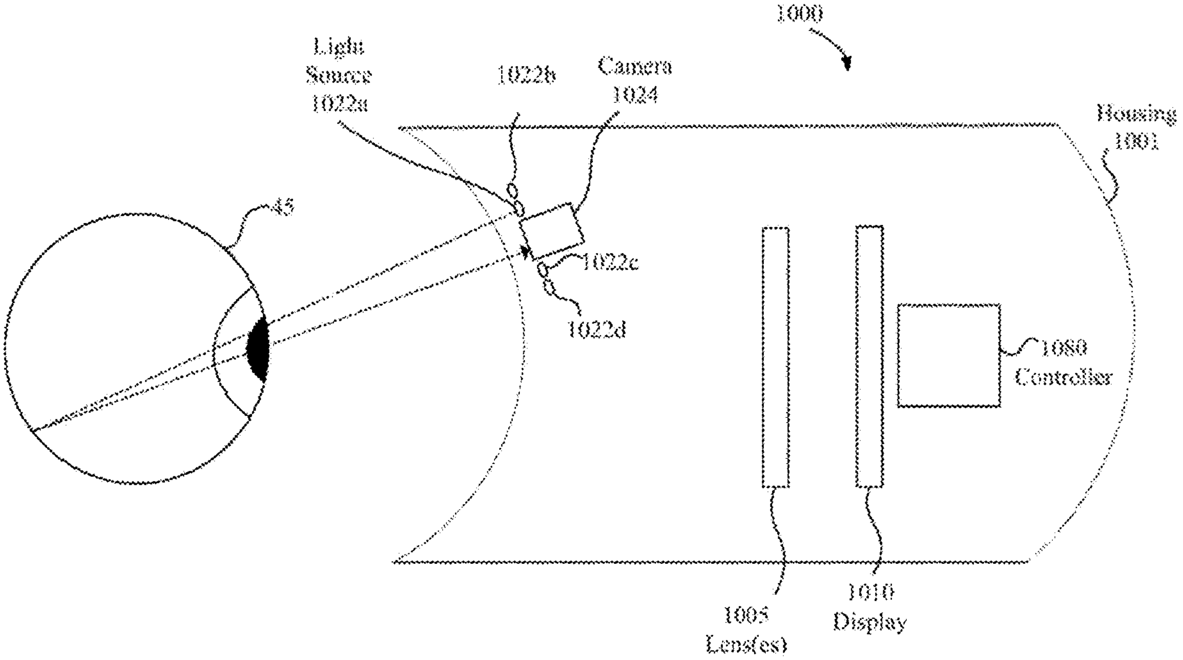
FIG. 8 is a block diagram of an example head-mounted device (HMD) in accordance with some implementations.

FIG. 8 illustrates a block diagram of an exemplary head-mounted device 1000 in accordance with some implementations. The head-mounted device 1000 includes a housing 1001 (or enclosure) that houses various components of the head-mounted device 1000. The housing 1001 includes (or is coupled to) an eye pad (not shown) disposed at a proximal (to the user 25) end of the housing 1001. In various implementations, the eye pad is a plastic or rubber piece that comfortably and snugly keeps the head-mounted device 1000 in the proper position on the face of the user 25 (e.g., surrounding the eye of the user 25).

The housing 1001 houses a display 1010 that displays an image, emitting light toward or onto the eye of a user 25. In various implementations, the display 1010 emits the light through an eyepiece having one or more lenses 1005 that refracts the light emitted by the display 1010, making the display appear to the user 25 to be at a virtual distance farther than the actual distance from the eye to the display 1010. For the user 25 to be able to focus on the display 1010, in various implementations, the virtual distance is at least greater than a minimum focal distance of the eye (e.g., 7 cm). Further, in order to provide a better user experience, in various implementations, the virtual distance is greater than 1 meter.

The housing 1001 also houses a tracking system including one or more light sources 1022, camera 1024, and a controller 1080. The one or more light sources 1022*a-d* emit light toward the eye 45 of the user that reflects and can be detected by the camera 1024. Based on the reflections, the controller 1080 can determine an eye tracking characteristic such as an eye accommodation characteristic of the user. In some implementations, the controller 1080 can determine a gaze direction and/or a blinking state (eyes open or eyes closed) of the user. As another example, the controller 1080 can determine a pupil center, a pupil size, or a point of regard. As another example, the controller 1080 can determine an eye accommodation characteristic of the user. Thus, in various implementations, the light is emitted by the one or more light sources 1022*a-d*, reflects off the eye 45 of the user, and is detected by the camera 1024. In various implementations, the light from the eye 45 of the user is reflected off a hot mirror or passed through an eyepiece before reaching the camera 1024.

The display 1010 emits light in a first wavelength range and the one or more light sources 1022*a-d* emit light in a second wavelength range. Similarly, the camera 1024 detects light in the second wavelength range. In various implementations, the first wavelength range is a visible wavelength range (e.g., a wavelength range within the visible spectrum of approximately 400-700 nm) and the second wavelength range is a near-infrared wavelength range (e.g., a wavelength range within the near-infrared spectrum of approximately 700-1400 nm).

In various implementations, eye tracking (or, in particular, a determined gaze direction and/or accommodation) is used to enable user interaction (e.g., the user 25 selects an option on the display 1010 by looking at it and focusing on it), provide foveated rendering (e.g., present a higher resolution in an area of the display 1010 the user 25 is looking at and a lower resolution elsewhere on the display 1010), or correct distortions (e.g., for images to be provided on the display 1010).

In various implementations, the camera 1024 is a frame/shutter-based camera that, at a particular point in time or multiple points in time at a frame rate, generates an image of the eye of the user 25. Each image includes a matrix of pixel values corresponding to pixels of the image which correspond to locations of a matrix of light sensors of the camera. In implementations, each image is used to measure or track pupil dilation by measuring a change of the pixel intensities associated with one or both of a user's pupils.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

As described above, one aspect of the present technology is the gathering and use of physiological data to improve a user's experience of an electronic device. The present disclosure contemplates that in some instances, this gathered data may include personal information data that uniquely identifies a specific person or can be used to identify interests, traits, or tendencies of a specific person. Such personal information data can include physiological data, demographic data, location-based data, telephone numbers, email addresses, home addresses, device characteristics of personal devices, or any other personal information.

The present disclosure recognizes that the use of such personal information data, in the present technology, can be used to the benefit of users. For example, the personal information data can be used to improve the content viewing experience. Accordingly, use of such personal information data may enable calculated control of the electronic device. Further, other uses for personal information data that benefit the user are also contemplated by the present disclosure.

The present disclosure further contemplates that the entities responsible for the collection, analysis, disclosure, transfer, storage, or other use of such personal information and/or physiological data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates implementations in which users selectively block the use of, or access to, personal information data. That is, the present disclosure contemplates that hardware or software elements can be provided to prevent or block access to such personal information data. For example, in the case of user-tailored content delivery services, the present technology can be configured to allow users to select to "opt in" or "opt out" of participation in the collection of personal information data during registration for services. In another example, users can select not to provide personal information data for targeted content delivery services. In yet another example, users can select to not provide personal information, but permit the transfer of anonymous information for the purpose of improving the functioning of the device.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences or settings based on non-personal information data or a bare minimum amount of personal information, such as the content being requested by the device associated with a user, other non-personal information available to the content delivery services, or publicly available information.

In some embodiments, data is stored using a public/private key system that only allows the owner of the data to decrypt the stored data. In some other implementations, the data may be stored anonymously (e.g., without identifying and/or personal information about the user, such as a legal name, username, time and location data, or the like). In this way, other users, hackers, or third parties cannot determine the identity of the user associated with the stored data. In some implementations, a user may access their stored data from a user device that is different than the one used to upload the stored data. In these instances, the user may be required to provide login credentials to access their stored data.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various objects, these objects should not be limited by these terms. These terms are only used to distinguish one object from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, objects, or components, but do not preclude the presence or addition of one or more other features, integers, steps, operations, objects, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:

at an electronic device having a processor and a light source:

illuminating the light source to direct light toward a retina of an eye;

receiving sensor data at a sensor, the sensor data corresponding to an illuminated spot on the retina; and determining an eye accommodation characteristic based on the sensor data, the eye accommodation characteristic determined based on a size or a position of the illuminated spot on the retina, wherein determining the eye accommodation characteristic comprises comparing a size or a position of an illuminated spot associated with a first point in time with a size or a position of a corresponding illuminated spot associated with a second point in time, wherein the size or the position of the illuminated spot associated with the first point in time and the size or the position of the corresponding illuminated spot associated with the second point in time are determined based on distinguishing other less-illuminated portions of the retina.

2. The method of claim 1, wherein the eye accommodation characteristic is determined during presentation of content via the electronic device.

3. The method of claim 1, wherein the light source comprises collimated illuminators that direct light toward multiple spots on the retina.

4. The method of claim 1, wherein an axis of the light produced using the light source is off-axis with respect to a lens of the eye.

5. The method of claim 1, wherein the sensor data comprises an image.

6. The method of claim 1, wherein determining the eye accommodation characteristic comprises determining that a change in eye accommodation has occurred.

7. The method of claim 1, wherein determining the eye accommodation characteristic comprises determining an eye accommodation state.

8. The method of claim 1, wherein determining the eye accommodation characteristic comprises comparing the size of the illuminated spot associated with the first point in time with the size of the corresponding illuminated spot associated with the second point in time, wherein divergence of the illuminated spots associated with the first and second points in time vary with time or location on the eye.

9. The method of claim 1, wherein determining the eye accommodation characteristic comprises comparing the position of the illuminated spot associated with the first point in time with the position of the corresponding illuminated spot associated with the second point in time.

10. The method of claim 1, wherein determining the eye accommodation characteristic comprises comparing relative positions of multiple illuminated spots associated with the first point in time with relative positions of corresponding illuminated spots associated with the second point in time.

11. The method of claim 1, wherein the size or position of the illuminated spot is determined via a machine-learning model.

12. The method of claim 1 further comprising determining an object upon which the eye is focused based on the eye accommodation characteristic.

13. The method of claim 1 further comprising positioning a virtual object in a graphical environment at a depth determined based on the eye accommodation characteristic.

14. The method of claim 1 further comprising tracking a gaze direction of the eye based on the eye accommodation characteristic.

15. A device comprising:

a light source;

a non-transitory computer-readable storage medium; and one or more processors coupled to the non-transitory computer-readable storage medium, wherein the non-transitory computer-readable storage medium comprises program instructions that, when executed on the one or more processors, cause the system to perform operations comprising:

illuminating the light source to direct light toward a spot on a retina of an eye;

receiving sensor data at a sensor, the sensor data corresponding to the illuminated spot on the retina; and determining an eye accommodation characteristic based on the sensor data, the eye accommodation characteristic determined based on a size or a position of the illuminated spot on the retina, wherein determining the eye accommodation characteristic comprises comparing a size or a position of an illuminated spot associated with a first point in time with a size or a position of a corresponding illuminated spot associated with a second point in time, wherein the size or the position of the illuminated spot associated with the first point in time and the size or the position of the corresponding illuminated spot associated with the second point in time are determined based on distinguishing other less-illuminated portions of the retina.

16. The device of claim 15, wherein the light source comprise collimated illuminators configured to illuminate multiple spots on the retina.

17. The device of claim 15, wherein determining the eye accommodation characteristic comprises determining that a change in eye accommodation has occurred.

18. The device of claim 15, wherein determining the eye accommodation characteristic comprises determining an eye accommodation state.

19. The device of claim 15, wherein the device is a head-mounted device (HMD).

20. A non-transitory computer-readable storage medium, storing computer-executable program instructions on a computer to perform operations comprising:

illuminating a light source to direct light toward a spot on a retina of an eye;

receiving sensor data at a sensor, the sensor data corresponding to the illuminated spot on the retina; and determining an eye accommodation characteristic based on the sensor data, the eye accommodation characteristic determined based on a size or a position of the illuminated spot on the retina, wherein determining the eye accommodation characteristic comprises comparing a size or a position of an illuminated spot associated with a first point in time with a size or a position of a corresponding illuminated spot associated with a second point in time, wherein the size or the position of the illuminated spot associated with the first point in time and the size or the position of the corresponding illuminated spot associated with the second point in time are determined based on distinguishing other less-illuminated portions of the retina.

21. The method of claim 1, wherein the position of the illuminated spot associated with the first point in time and the position of the corresponding illuminated spot associated with the second point in time are determined based on images of the eyes including the illuminated spot and corresponding illuminated spot that are captured via an eye tracking system.

22. The method of claim 1, wherein the position of the illuminated spot associated with the first point in time and the position of the corresponding illuminated spot associated with the second point in time are determined via an algorithm.

23. The method of claim 1, wherein the position of the illuminated spot associated with the first point in time and the position of the corresponding illuminated spot associated with the second point in time are determined via an algorithm that uses a threshold.

24. The method of claim 1, wherein the position of the illuminated spot associated with the first point in time and the position of the corresponding illuminated spot associated with the second point in time are determined via a machine learning model.

25. The method of claim 1, wherein the size or the position of the illuminated spot associated with the first point in time and the size or the position of the corresponding illuminated spot associated with the second point in time are determined based on a pixel brightness threshold.

26. The method of claim 1, wherein the size or the position of the illuminated spot associated with the first point in time and the size or the position of the corresponding illuminated spot associated with the second point in time are determined based on relationships to nearby pixels.

* * * * *